(12) United States Patent
Zacharias et al.

(10) Patent No.: US 9,713,523 B2
(45) Date of Patent: *Jul. 25, 2017

(54) SYSTEM AND METHOD OF PIVOTED STENT DEPLOYMENT

(71) Applicant: TRIVASCULAR, INC., Santa Rosa, CA (US)

(72) Inventors: Isaac J. Zacharias, Santa Rosa, CA (US); Diego Aristizabal, Santa Rosa, CA (US); Michael Mohn, Maple Grove, MN (US); Michael V. Chobotov, Santa Rosa, CA (US)

(73) Assignee: TRIVASCULAR, INC., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/452,343

(22) Filed: Aug. 5, 2014

(65) Prior Publication Data

US 2014/0350656 A1 Nov. 27, 2014

Related U.S. Application Data

(60) Division of application No. 13/277,117, filed on Oct. 19, 2011, now abandoned, which is a continuation of
(Continued)

(51) Int. Cl.
*A61F 2/06* (2013.01)
*A61F 2/07* (2013.01)
(Continued)

(52) U.S. Cl.
CPC .................. *A61F 2/07* (2013.01); *A61F 2/91* (2013.01); *A61F 2/915* (2013.01); *A61F 2/95* (2013.01);
(Continued)

(58) Field of Classification Search
CPC ................ A61F 2/07; A61F 2002/9505; A61F 2002/9511; A61F 2002/9534
See application file for complete search history.

(56) References Cited

U.S. PATENT DOCUMENTS 5,534,007 A   7/1996 St. Germain et al.
5,662,703 A   9/1997 Yurek et al.
(Continued)

FOREIGN PATENT DOCUMENTS

EP           0621016      10/1994
WO    WO 2005/115275    12/2005
(Continued)

OTHER PUBLICATIONS

Extended European Search Report dated: Nov. 9, 2015 in European Application No. EP 13772199.9 filed: Mar. 29, 2013.
(Continued)

*Primary Examiner* — Jacqueline Woznicki
(74) *Attorney, Agent, or Firm* — Schmeiser, Olsen & Watts LLP; William Anderson

(57) ABSTRACT

The invention provides a stent-graft system comprising a graft member and a stent having a connection end interconnected with the graft member and a free end opposed thereto. A belt retaining structure is provided at the stent free end. A belt is releasably retained in the belt retaining structure and is configured to constrain the stent free end independent of the stent connection end. A method of securing at least one end of a stent-graft within a vessel is also provided.

8 Claims, 7 Drawing Sheets

Related U.S. Application Data application No. 11/861,716, filed on Sep. 26, 2007, now Pat. No. 8,066,755.

(51) Int. Cl.
*A61F 2/91* (2013.01)
*A61F 2/915* (2013.01)
*A61F 2/95* (2013.01)
*A61F 2/848* (2013.01)
*A61F 2/89* (2013.01)

(52) U.S. Cl.
CPC .............. *A61F 2/848* (2013.01); *A61F 2/89* (2013.01); *A61F 2002/075* (2013.01); *A61F 2002/91558* (2013.01); *A61F 2002/9505* (2013.01); *A61F 2002/9511* (2013.01); *A61F 2002/9534* (2013.01); *A61F 2220/0016* (2013.01); *A61F 2230/005* (2013.01); *A61F 2230/0054* (2013.01); *A61F 2230/0067* (2013.01)

(56) References Cited

U.S. PATENT DOCUMENTS

| | | | | |
|---|---|---|---|---|
| 5,776,142 | A | * | 7/1998 | Gunderson ............... A61F 2/88 606/108 |
| 6,582,460 | B1 | | 6/2003 | Cryer |
| 7,604,661 | B2 | | 10/2009 | Pavcnik et al. |
| 7,998,189 | B2 | | 8/2011 | Kolbel et al. |
| 9,364,314 | B2 | | 6/2016 | Berra et al. |
| 2002/0151953 | A1 | * | 10/2002 | Chobotov ............... A61F 2/954 623/1.11 |
| 2002/0151956 | A1 | * | 10/2002 | Chobotov ............... A61F 2/07 623/1.12 |
| 2002/0188344 | A1 | * | 12/2002 | Bolea ....................... A61F 2/90 623/1.11 |
| 2003/0199967 | A1 | | 10/2003 | Hartley et al. |
| 2004/0138734 | A1 | * | 7/2004 | Chobotov ............... A61F 2/954 623/1.11 |
| 2004/0193252 | A1 | | 9/2004 | Perez et al. |
| 2004/0210301 | A1 | | 10/2004 | Obermiller |
| 2005/0033406 | A1 | * | 2/2005 | Barnhart ................... A61F 2/07 623/1.13 |
| 2006/0111770 | A1 | | 5/2006 | Pavcnik et al. |
| 2006/0142846 | A1 | | 6/2006 | Pavcnik et al. |
| 2006/0178732 | A1 | * | 8/2006 | Chobotov ................ A61F 2/07 623/1.34 |
| 2008/0264102 | A1 | | 10/2008 | Berra |
| 2009/0082845 | A1 | * | 3/2009 | Chobotov ................ A61F 2/07 623/1.13 |
| 2009/0082847 | A1 | * | 3/2009 | Zacharias ................ A61F 2/82 623/1.15 |
| 2009/0287290 | A1 | | 11/2009 | Macaulay et al. |
| 2009/0326640 | A1 | * | 12/2009 | Yoshimura ............... A61F 2/07 623/1.15 |
| 2010/0016943 | A1 | * | 1/2010 | Chobotov ................ A61F 2/07 623/1.11 |
| 2010/0161028 | A1 | | 6/2010 | Chuter et al. |
| 2010/0324651 | A1 | * | 12/2010 | Holzer ..................... A61F 2/90 623/1.15 |
| 2013/0268044 | A1 | | 10/2013 | Parsons et al. |
| 2013/0268048 | A1 | * | 10/2013 | Watson ..................... A61F 2/95 623/1.11 |
| 2013/0268056 | A1 | | 10/2013 | Chobotov et al. |
| 2013/0268057 | A1 | | 10/2013 | Vinluan et al. |

FOREIGN PATENT DOCUMENTS

| | | |
|---|---|---|
| WO | WO 2010/127040 | 11/2010 |
| WO | WO 2017/019913 | 2/2017 |

OTHER PUBLICATIONS

Extended European Search Report dated Oct. 8, 2015 in European Application No. EP 13771941.5 filed: Apr. 1, 2013.
Extended European Search Report dated: Jan. 27, 2015 in European Application No. EP 11841183.4 filed: Nov. 15, 2011.
Supplemental European Search Report dated: Feb. 13, 2015 in European Application No. EP 11841183.4 filed: Nov. 15, 2011.
International Search Report and Written Opinion dated: Dec. 1, 2016 in International Patent Application No. PCT/US2016/044583 filed: Jul. 28, 2016 and published as: WO/2017/019913 on: Feb. 2, 2017.

* cited by examiner

SYSTEM AND METHOD OF PIVOTED STENT DEPLOYMENT

RELATED APPLICATIONS

This application is a divisional application of U.S. patent application Ser. No. 13/277,117, titled "System and Method of Pivoted Stent Deployment", filed Oct. 19, 2011, by Isaac J. Zacharias et al., which is a continuation of U.S. patent application Ser. No. 11/861,716, now U.S. Pat. No. 8,066,755, titled "System and Method of Pivoted Stent Deployment", filed Sep. 26, 2007, by Isaac J. Zacharias et al., which are both incorporated by reference herein in their entirety.

BACKGROUND OF THE INVENTION

The present invention relates to a system for the treatment of disorders of the vasculature. More specifically, the invention relates to a system for the treatment of disease or injury that potentially compromises the integrity of a flow conduit in the body. For example, an embodiment of the invention is useful in treating indications in the digestive and reproductive systems as well as indications in the cardiovascular system, including thoracic and abdominal aortic aneurysms, arterial dissections (such as those caused by traumatic injury), etc.

For indications such as abdominal aortic aneurysms, traditional open surgery is still the conventional and most widely-utilized treatment when the aneurysm's size has grown to the point that the risk of aneurysm rupture outweighs the drawbacks of surgery. Surgical repair involves replacement of the section of the vessel where the aneurysm has formed with a graft. An example of a surgical procedure is described by Cooley in Surgical Treatment of Aortic Aneurysms, 1986 (W. B. Saunders Company).

Despite its advantages, however, open surgery is fraught with high morbidity and mortality rates, primarily because of the invasive and complex nature of the procedure. Complications associated with surgery include, for example, the possibility of aneurysm rupture, loss of function related to extended periods of restricted blood flow to the extremities, blood loss, myocardial infarction, congestive heart failure, arrhythmia, and complications associated with the use of general anesthesia and mechanical ventilation systems. In addition, the typical patient in need of aneurysm repair is older and in poor health, facts that significantly increase the likelihood of complications.

Due to the risks and complexities of surgical intervention, various attempts have been made to develop alternative methods for treating such disorders. One such method that has enjoyed some degree of success is the catheter-based delivery of a stent-graft via the femoral arteries to exclude the aneurysm from within the aorta. Illustrative stent-grafts and methods of delivery thereof are described in U.S. Patent Application Publication Nos. 2003/0125797A1, 2004/0138734A1 and U.S. Pat. No. 6,295,019, each of which is incorporated herein in its entirety by reference herein.

SUMMARY OF THE INVENTION

In one aspect, the invention provides a stent-graft system comprising a graft member and a stent having a connection end interconnected with the graft member and a free end opposed thereto. A belt retaining structure is provided at the stent free end. A belt is releasably retained in the belt retaining structure and is configured to constrain the stent free end independent of the stent connection end.

In another aspect, the invention provides a method of securing at least one end of a graft within a vessel. The method comprises: positioning within the vessel a stent-graft comprising a stent and a graft with a connection end of the stent connected to an end of the graft, the stent having a free end opposite the connection end, the stent free end including a belt retaining structure with a belt releasably retained thereabout; deploying the stent connection end within the vessel; repositioning the stent-graft within the vessel; and releasing the belt to deploy the free end of the stent.

Other aspects and advantages of the present invention will be apparent from the detailed description of the invention provided hereinafter.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
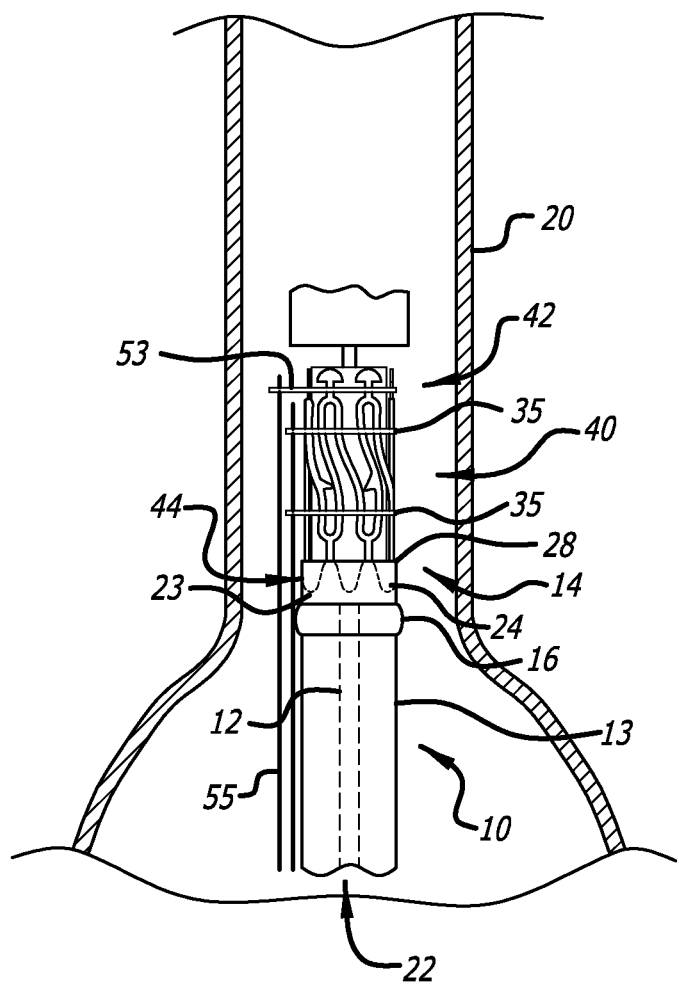
FIG. 1 shows a portion of an endovascular graft according to an embodiment of the present invention in a contracted state for delivery through a catheter.

Referring to FIG. 1, a portion of an illustrative endovascular graft 10 is shown in its contracted configuration. Unless otherwise stated, the term "graft" or "endovascular graft" is used herein to refer to a prosthesis capable of repairing and/or replacing diseased vessels or portions thereof, including generally tubular and bifurcated devices and any components attached or integral thereto. For purposes of illustration, the graft embodiments described herein may be used in the endovascular treatment of abdominal aortic aneurysms (AAA) or thoracic aortic aneurysms, however, other applications are within the scope of the present invention. For the purposes of this application, with reference to endovascular graft devices, the term "proximal" describes the end of the graft that will be oriented towards the oncoming flow of bodily fluid, typically blood, when the device is deployed within a body passageway. The term "distal" therefore describes the graft end opposite the proximal end. Finally, while the drawings in the various figures are accurate representations of the various embodiments of the present invention, the proportions of the various components thereof are not necessarily shown to exact scale within and among or between any given figure(s).

An end of the graft 10 is illustrated and may represent the proximal or distal end of the graft 10. The graft 10 includes a generally tubular structure or graft body section 13 comprised of one or more layers of fusible material, such as expanded polytetrafluoroethylene (ePTFE). An inflatable cuff 16 is disposed at or near the end 14 of graft body section 13. A neck portion 23 is disposed in the vicinity of graft body section end 14 and serves as an additional means to help seal the deployed graft against the inside of a body passageway. Graft body section 13 forms a longitudinal lumen 22 configured to confine a flow of fluid therethrough.

A attachment ring 24 is affixed to or integrally formed in graft body section 13, or as shown in FIG. 1, at or near graft body section end 14 and neck portion 23. In the embodiment of FIG. 1, attachment ring 24 is a serpentine ring structure comprising apices 28. Other embodiments of attachment ring 24 may take different configurations. Attachment ring 24 may be made from any suitable material that permits expansion from a constrained state, most usefully a shape memory alloy having superelastic properties such as nickel titanium (NiTi). Other suitable attachment ring 24 materials include stainless steel, nickel-cobalt alloys such as MP35N, tantalum and its alloys, polymeric materials, composites, and the like. Attachment ring 24 (as well as all stents and attachment rings described herein) may be configured to self-expand from the illustrated radially constrained state.

Figure 5:
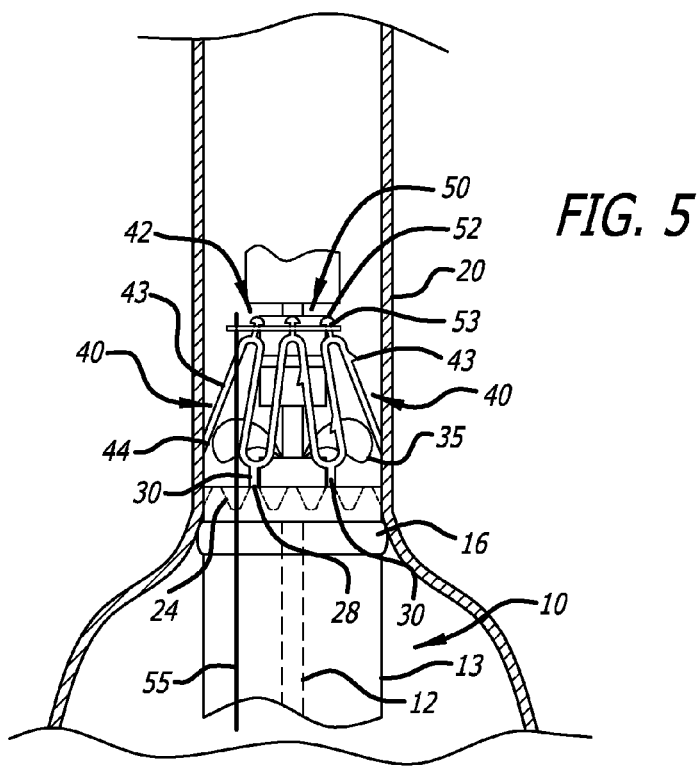
FIG. 5 shows a portion of an endovascular graft according to an embodiment of the present invention partially deployed within the internal vasculature of the patient.
Figure 6:
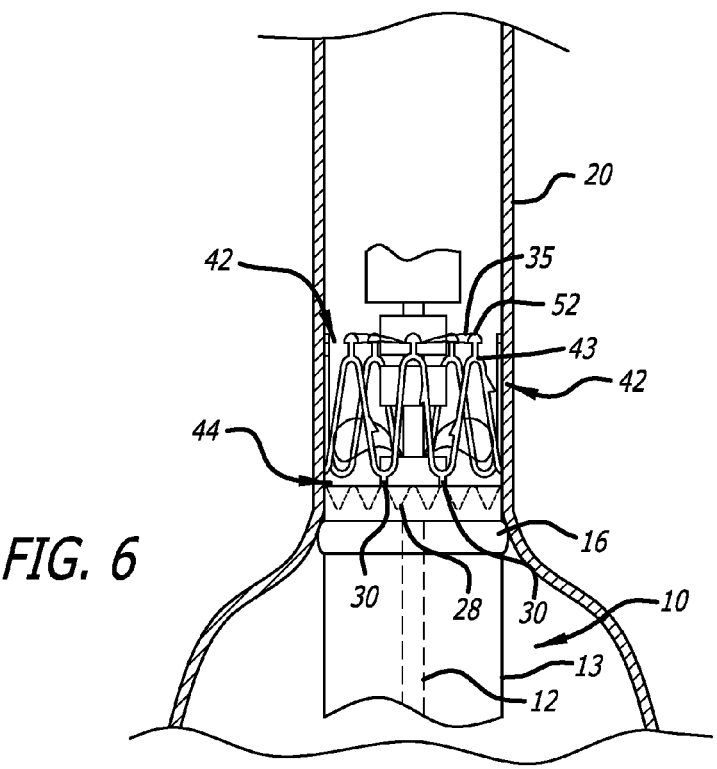
FIG. 6 shows the endovascular graft portion of FIG. 5 fully deployed within the internal vasculature of the patient.

Some apices 28 may also comprise an attachment ring connector element 30 (see FIGS. 5 and 6). The number of connector elements 30 may vary and can be distributed, for example, on every apex, every third or fourth apex, or any other pattern are within the scope of the present invention.

Graft 10 further comprises one or more stents 40 having, in the deployed state (see FIG. 6), a generally free end 42 and a connection end 44. FIGS. 1 and 5-6 illustrate a proximal stent 40, but the stents 40 may additionally or alternatively be provided on the distal end of the graft 10. In the case of a bifurcated graft, a stent 40 may be provided on the distal end of each leg of the bifurcated graft.

As shown in FIGS. 1 and 5-6, stent 40 is typically, though not necessarily, made a part of graft 10 by having the connection end 44 affixed or connected to attachment ring 24 via connector elements as described in detail below. The connection end 44 of stent 40 may also be affixed or embedded directly to or in neck portion 23 and/or other portions of graft body section 13. In addition, the attachment ring and the stent may not be mechanically or otherwise fastened to one another but rather unified, formed of a monolithic piece of material, such as NiTi.

This configuration of stent 40, attachment ring 24, neck portion 23, and cuff 16 helps to separate the sealing function of cuff 16, which requires conformation and apposition to the vessel wall within which graft 10 is deployed without excessive radial force, from the anchoring function of stent 40 (attachment ring 24 and neck portion 23 play intermediate roles). As will be described in more detail hereinafter, the stents 40 of the present invention permit improved positioning of the graft 10 prior to stent anchoring, thereby facilitating better placement and sealing of the graft 10.

Figure 2:
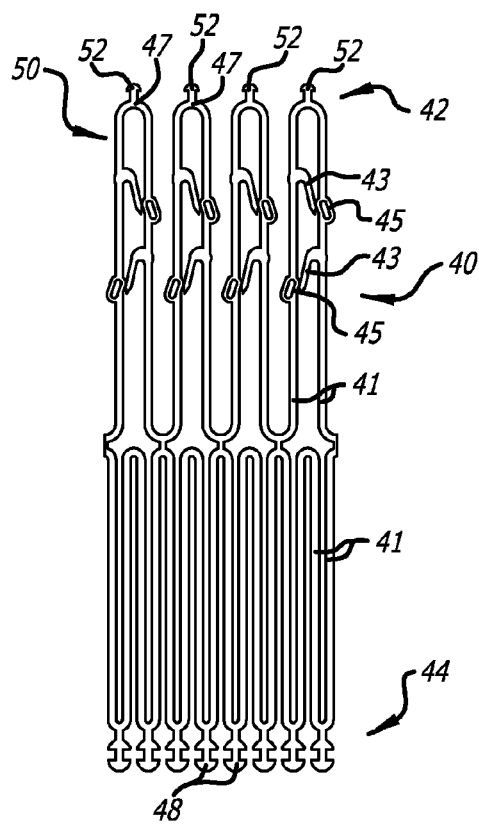
FIG. 2 shows a flat pattern of an embodiment of a stent in accordance with the present invention.
Figure 3:
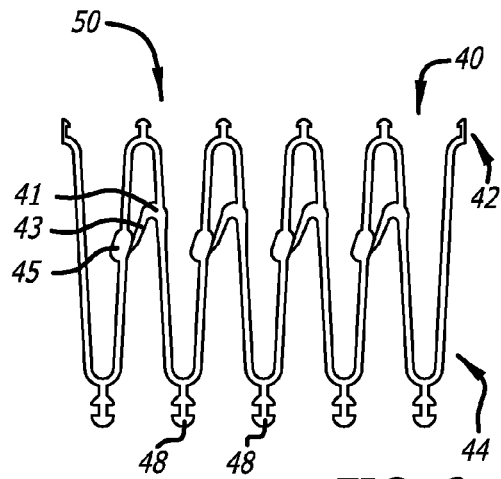
FIG. 3 shows a flat pattern of an alternative embodiment of a stent in accordance with the present invention.
Figure 4:
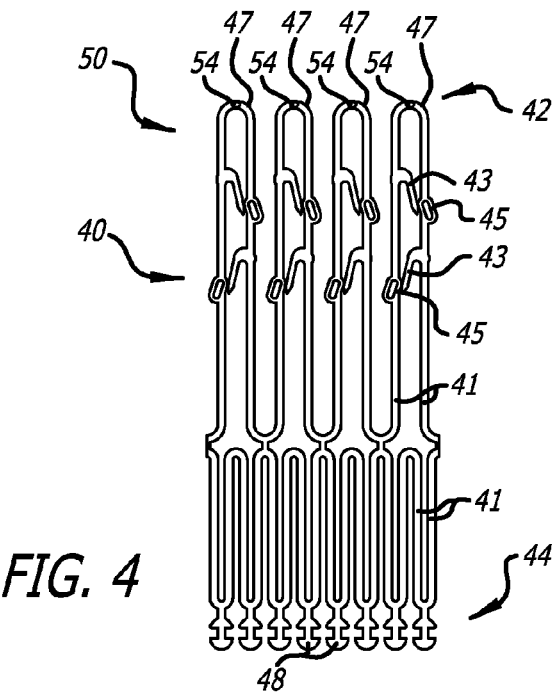
FIG. 4 shows a flat pattern of another alternative embodiment of a stent in accordance with the present invention.

Referring to FIGS. 2-4, each stent 40 of the present invention generally comprises a series of interconnected struts 41. As illustrated, the struts 41 can have various configurations and lengths. Each stent 40 further comprises stent connector elements 48 at the connection end 44 thereof. The stent connector elements 48 are configured to be affixed or otherwise connected to attachment ring connector elements 30 via coupling members (not shown), for example, threads or wires. The stents 40 may be manufactured from any suitable material, including the materials suitable for attachment ring 24. When manufactured from a shape memory alloy having superelastic properties such as NiTi, the stents 40 may be configured to self-expand upon release from the contracted state. The strut structure is often formed as a flat structure, as illustrated in FIGS. 2-4, and thereafter, wrapped and connected in a cylindrical or other configuration, as illustrated in FIG. 1.

Each stent 40 includes one or more barbs 43. A barb 43 can be any outwardly directed protuberance, typically terminating in a sharp point that is capable of at least partially penetrating a body passageway in which graft 10 is deployed (typically the initial and medial layers of a blood vessel such as the abdominal aorta). The number of barbs, the length of each barb, each barb angle, and the barb orientation may vary from barb to barb within a single stent 40 or between multiple stents 40 within a single graft. Although the various barbs 43 (and tuck pads 45 discussed below) may be attached to or fixed on the stent struts 41, it is preferred that they be integrally formed as part of the stent struts 41, as shown in the various figures.

When stent 40 is deployed in the abdominal aorta, for example, typically in a location proximal to the aneurysm and any diseased tissue, barbs 43 are designed to work in conjunction with the distally-oriented blood flow field in this location to penetrate tissue and prevent axial migration of graft 10. As such, the barbs 43 in the FIG. 1 embodiment are oriented distally with respect to graft body section 13. However, the number, dimensions, configuration and orientation of barbs 43 may vary significantly, yet be within the scope of the present invention.

Struts 41 may also comprise optional integral tuck pads 45 disposed opposite each barb 43. During preparation of graft 10 (and therefore the stents 40) into its reduced diameter delivery configuration, each barb 43 is placed behind a corresponding strut 41 and/or optional tuck pad 45, if present, to thereby prevent the barbs 43 from contacting the inside of a delivery sheath or catheter during delivery of the device and from undesired contact with the inside of a vessel wall. As described in U.S. Pat. No. 6,761,733 to Chobotov et al., the complete disclosure of which is incorporated herein by reference, an initial stage release belt 35 disposed about the struts 41 retain the stent 40 in this delivery configuration. The initial stage release belts 35 retain the contracted stent 40 on a guidewire chassis 12 or the like.

The number of initial stage belts 35 varies in accordance with the structure of the stent 40. For example, the stents 40 as illustrated in FIGS. 2 and 4 have proximal and distal segments and two corresponding initial stage belts 35, one about the proximal segment and one about the distal segment, are used to secure the stent 40 as shown in FIG. 1. In shorter stents 40 having a single segment, like the stent 40 illustrated in FIG. 3, a single initial stage belt 35 is typically used to secure the stent 40. Upon deployment of the stent 40, by releasing the initial stage belt(s) 35, the radial expansion of stent 40 results in a displacement of struts 41 so that the distance between them increases. As the struts 41 separate, the barbs 43 are freed from behind the struts 41 and optional tuck pads 45, if present, and engage the wall of the vessel being treated. To enhance the engagement of the barbs 43 in the vessel wall 20, the barbs 43 may be designed to work in conjunction with the distally-oriented blood flow field, that is, the barbs 43 are oriented distally, however, they do not have to be. In the illustrative embodiment, the barbs 43 at the proximal end are oriented distally, while the barbs 43 at the distal end are oriented proximally.

While secure engagement of the barbs 43 in the vessel wall 20 is desirable to prevent axial migration of graft 10, such engagement is generally permanent and not subject to modification. Attempts to reposition the stent 40 or graft 10 after engagement of the barbs 43 in the vessel wall 20 may cause tearing or other damage to the vessel wall 20.

Referring to FIGS. 2-4, each stent 40 of the present invention includes a belt retaining structure 50 provided along the crowns 47 at the free end 42 of the stent 40. In the embodiments illustrated in FIGS. 2 and 3, the belt retaining structure 50 includes a plurality of mushroom shaped connectors 52 extending from the crowns 47. The mushroom shaped connectors 52 may be provided at each crown 47, as illustrated, or in any configuration with respect to the crowns 47. Referring to FIGS. 1 and 5, a releasable secondary stage belt 53 is positionable about the mushroom shaped connectors 52 to retain the stent free end 42 in a contracted state until the secondary stage belt 53 is released, for example, via a release wire 55. In the embodiment illustrated in FIG. 4, the belt retaining structure 50 includes a through hole 54 provided in a plurality of the crowns 47. A releasable belt (not shown) is threaded through the through holes 54 and pulled tight to retain the stent free end 42 in a contracted state until the belt is released. Other belt retaining structures 50 along the stent free end 42 may also be utilized.

As shown in FIG. 5, upon release of the initial stage belts 35, the stent connection end 44, the attachment ring 24, and the graft 10 expand while the secondary stage belt 53 engages the belt retaining structure 50 and retains the stent free end 42 in the generally contracted condition. The stent connection end 44 and the graft 10 expand based on the self expanding nature of the stent 40 and also the force of the distal fluid flow into the graft 10. The struts 41 and barbs 43 are configured such that when the belt retaining structure 50 is in place and the stent free end 42 is restrained, the barbs 43 do not extend sufficiently radially to engage the vessel wall 20, but instead remain spaced therefrom. As such, the graft 10 and stent 40 may be moved and repositioned without the barbs 43 engaging and damaging the vessel wall 20. In at least one embodiment of the invention, the barbs 43 are axially positioned closer to the stent free end 42 than the stent connection end 44 to further ensure the barbs 43 will not contact the vessel wall 20 in the partially deployed state.

Once the stent 40 and graft 10 are positioned as desired, the release wire 55 may be pulled to release the secondary stage belt 53 from the belt retaining structure 50, thereby allowing the stent 40 to fully deploy as illustrated in FIG. 6. Upon full deployment, the struts 41 are free to fully radially expand such that the barbs 43 engage the vessel wall 20 in a normal manner.

In addition to facilitating manual movement and repositioning of the graft 10 and stent 40, the staged deployment of the stent 40 also facilitates self-alignment of the stent 40 and graft 10. As explained above, upon release of the initial stage belts 35, the graft 10 is free to expand and distal fluid flow flows into the graft 10 and creates a "windsock" effect. That is, the distal fluid flow expands the graft 10 and applies a slight distal force upon the graft 10. This distal force helps to align the graft 10 and the stent 40 within the vessel.

Figure 7:
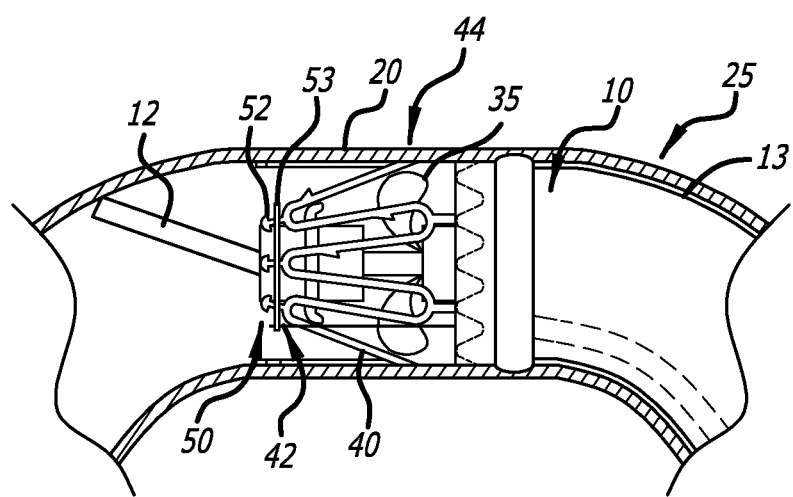
FIG. 7 shows a portion of an endovascular graft according to an embodiment of the present invention partially deployed within an aortic arch of the patient.
Figure 8:
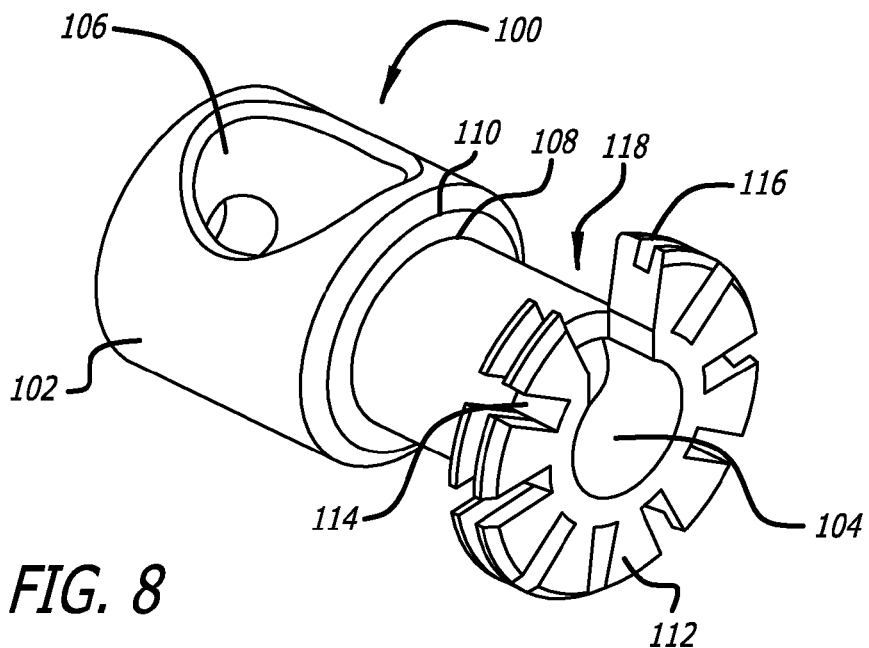
FIG. 8 is an isometric view of a pivot fitting in accordance with another embodiment of the present invention.
Figure 9:
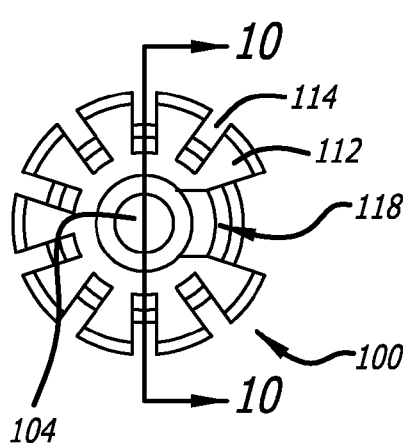
FIG. 9 is an end view of the pivot fitting of FIG. 8.
Figure 10:
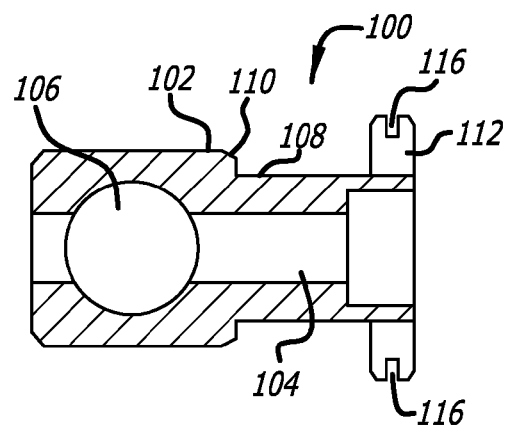
FIG. 10 is a cross-sectional view along the line 10-10 in FIG. 9.

This self alignment is particularly advantageous during deployment of a stent graft within an angulated vessel, for example, in the aortic arch. Referring to FIG. 7, the stent 40 is illustrated partially deployed in an aortic arch 25. The delivery guidewire chassis 12 contacts the vessel wall 20 and does not remain coaxial with respect to the arch 25. As such, in the initial delivery position, the stent 40 may be cocked or otherwise misaligned with respect to the vessel wall 20. In a prior art single stage deployment, the stent would expand and the barbs would engage the vessel wall even if the stent was misaligned. With the stent 40 of the present invention, the initial stage belt(s) 35 are released and the stent 40 is partially deployed. The distal fluid flow flows into the graft 10 and creates the windsock effect, thereby pulling the graft 10 and stent 40 into alignment with the flow and thereby the vessel wall 20.

Referring to FIGS. 8-13, a pivot fitting 100 configured to assist in the multi-staged deployment of stent 40 will be described. The pivot fitting 100 has a generally cylindrical body 102 with an axial through bore 104 configured to position the fitting 100 about the guidewire chassis 12 (see FIG. 13) or the like. A transverse bore 106 is provided to facilitate positioning and attachment of the pivot fitting 100 about the guidewire chassis 12 and loading into the delivery catheter (not shown).

The pivot fitting 100 includes an area 108 of reduced cross section extending between a shoulder 110 and a radial belt support member 112. The area 108 is configured to receive the free ends of the stent 40, for example, the mushroom shaped connectors 52 or the crowns 47 with through holes 54. To facilitate passage of the stent members, the radial belt support member 112 includes a plurality of radial slots 114. In the embodiment illustrated in FIG. 13, each radial slot 114 receives the narrow neck portion of a respective mushroom shaped connector 52.

A circumferential groove 116 is provided along the radial surface of the radial belt support member 112. The circumferential groove 116 is configured to receive and maintain the secondary stage belt 53. A belt radial slot 118 is provided in the radial belt support member 112 to facilitate passage of the secondary stage belt 53 from the guidewire chassis 12 or the like outward to the circumferential groove 116.

Figure 11:
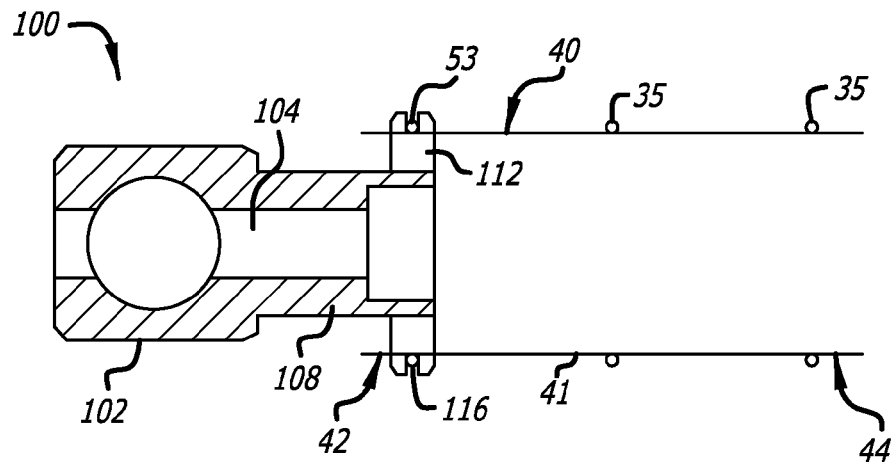
FIG. 11 is a cross-sectional view similar to FIG. 10 illustrating schematically a stent thereon in a contracted state.
Figure 12:
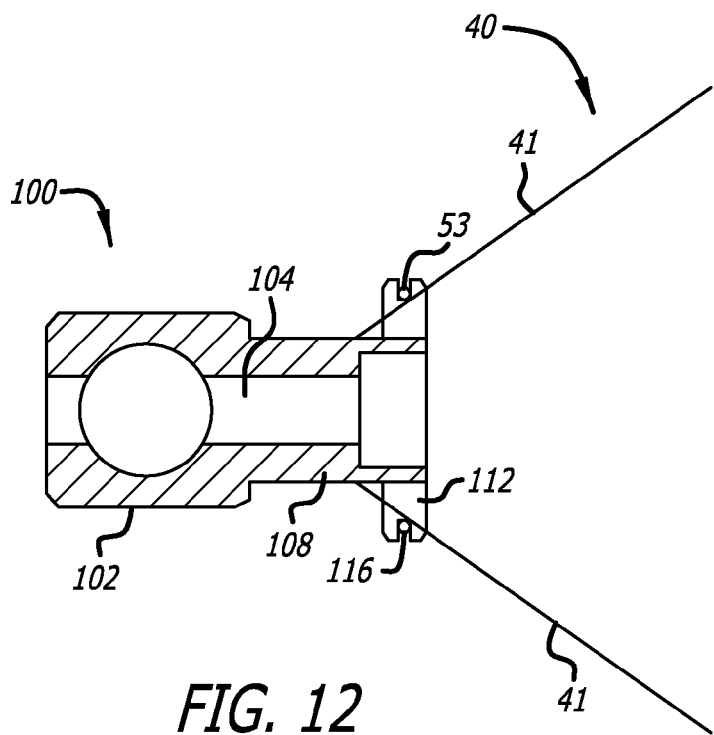
FIG. 12 is a cross-sectional view similar to FIG. 10 illustrating schematically a stent thereon in a partially deployed state.
Figure 13:
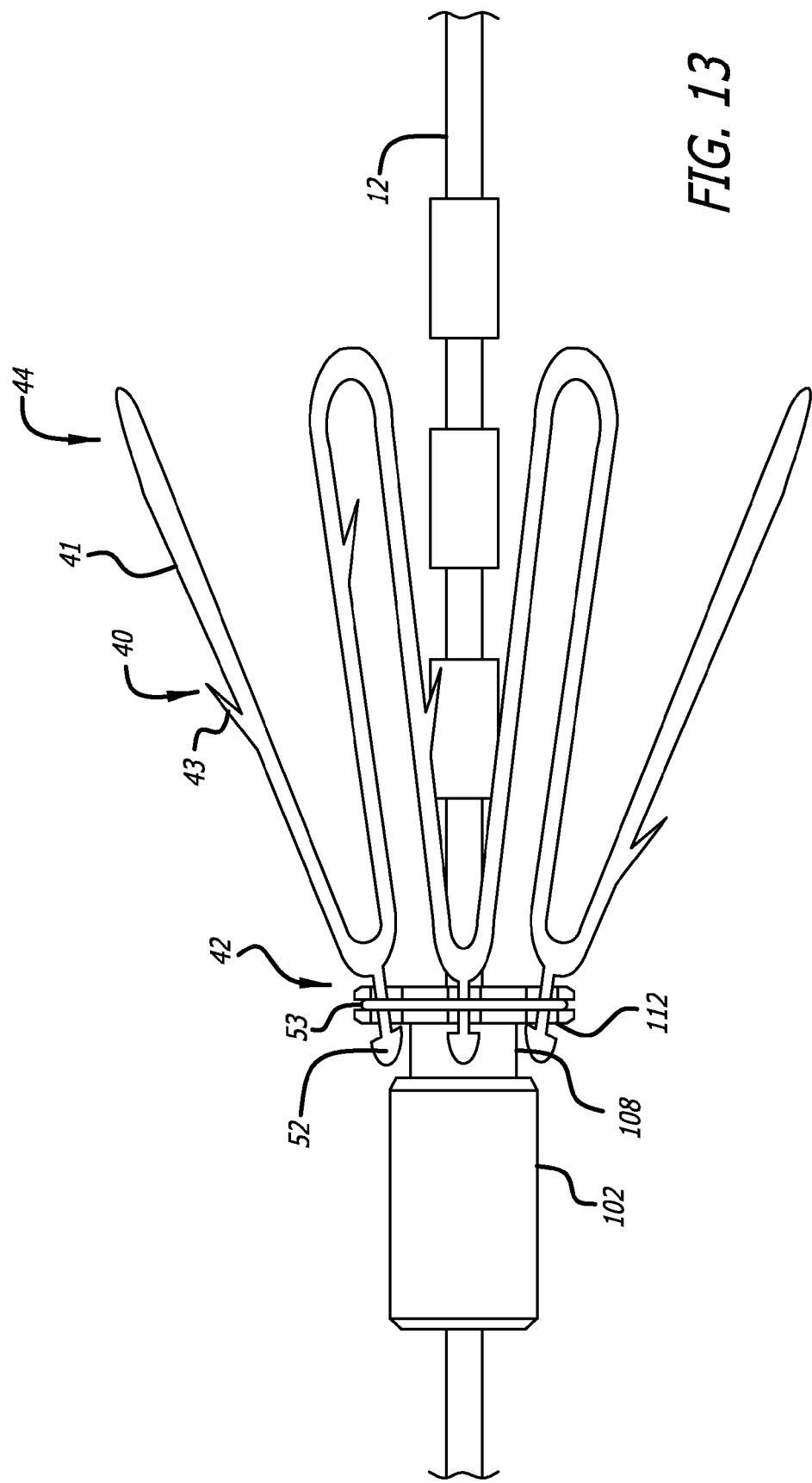
FIG. 13 is a perspective view illustrating a stent in the partially deployed state of FIG. 12.

Referring to FIG. 11, in the delivery stage, the stent 40 is compacted with the free end 42 passing through the radial slots 114 in the radial belt support member 112. The secondary stage belt 53 is secured in the circumferential groove 116 and constrains the stent free end 42. Turning to FIGS. 12 and 13, upon release of the initial stage release belts 35, the connection end 44 of the stent 40 expands while the free end 42 is retained by the secondary stage belt 53. The opening diameter of the connection end 44 can be controlled by the relation of the outer diameter of area 108 and the inner diameter of the circumferential groove 116 and the length of the portion of the stent free end 42 that extends into area 108. In this partially deployed state, the stent free end 42 is securely retained by the pivot fitting 100, which in turn is connected to the guidewire chassis 12. As such, movement of the guidewire chassis 12 provides relatively precise control of the position of the stent 40. Once the stent 40 is positioned in a desired position, the secondary stage belt 53 is released and the stent free end 42 disengages from the pivot fitting 100 and expands. The pivot fitting 100 remains connected to the guidewire chassis 12 and is removed upon removal thereof.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. A method of deploying a stent-graft within a vessel, comprising:

positioning within the vessel a stent-graft in a contracted state, the stent-graft comprising a stent and a graft with a connection end of the stent connected to an end of the graft, the stent including a series of interconnected struts disposed between respective crowns at the connection end and crowns disposed at a free end of the stent opposite the connection end, the stent free end including a belt retaining structure comprising a through hole provided in a plurality of crowns of the stent at the free end thereof and a belt releasably threaded through the through holes with the belt retaining the stent free end in a contracted state;

releasing the stent connection end from the contracted state within the vessel so as to allow the stent connection end to expand while the stent free end remains in the contracted state; and thereafter releasing the belt from the through holes in the crowns of the free end and allowing the free end of the stent to expand.

2. The method of claim 1 wherein positioning the stent-graft within the vessel comprises positioning the stent-graft within a thoracic aorta.

3. The method of claim 1 wherein positioning the stent-graft within the vessel comprises positioning the stent-graft within an abdominal aorta.

4. The method of claim 1 wherein releasing the stent connection end within the vessel includes releasing an initial stage release belt which constrains the stent connection end.

5. The method of claim 1 further comprising repositioning the stent-graft within the vessel after release of the stent connection end but prior to release of the stent free end.

6. The method of claim 5 wherein repositioning the stent-graft within the vessel includes moving the stent, the graft or a combination of the stent and the graft.

7. The method of claim 5 wherein repositioning the stent-graft within the vessel includes allowing a fluid flow through the vessel to enter within the graft to self-align the stent and graft.

8. The method of claim 1 wherein releasing the belt from the through holes comprises pulling a release wire from the belt.

* * * * *